United States Patent [19]

Gante et al.

[11] Patent Number: 5,215,967
[45] Date of Patent: Jun. 1, 1993

[54] AMINOACID DERIVATIVES INHIBITING RENIN

[75] Inventors: Joachim Gante; Peter Raddatz; Johannes Sombroek, all of Darmstadt; Claus J. Schmitges, Gross-Umstadt; Klaus O. Minck, Ober-Ramstadt, all of Fed. Rep. of Germany

[73] Assignee: Merck Patent Gesellschaft mit beschrankter Haftung, Darmstadt, Fed. Rep. of Germany

[21] Appl. No.: 443,530

[22] Filed: Nov. 30, 1989

[30] Foreign Application Priority Data

Nov. 30, 1988 [DE] Fed. Rep. of Germany ....... 3840289

[51] Int. Cl.$^5$ ...................... A61K 37/00; C07K 5/00
[52] U.S. Cl. ........................ 514/18; 514/19; 530/331; 530/800
[58] Field of Search ............... 514/18, 19; 530/331, 530/800

[56] References Cited

U.S. PATENT DOCUMENTS 4,841,067 6/1989 Iizuka et al.

FOREIGN PATENT DOCUMENTS 0081783 6/1982 European Pat. Off.
77028 4/1983 European Pat. Off.
WO88/05050 7/1988 European Pat. Off.
3619508 12/1987 Fed. Rep. of Germany.
84/03044 8/1984 World Int. Prop. O.

OTHER PUBLICATIONS

Bolis et al., "Renin Inhibitors ... Dipeptides Analogues ...", J. Med. Chem. 1987, 30, 1729-1737.
Denkewalter et al., "Progress in Drug Research", vol. 10, 1966, pp. 510-512.
Burger, "Medicinal Chemistry", 2nd Ed, 1960, pp. 565-571, 578-581, 600-601.
Haber et al., "Renin Inhibitors: A Search for Principles of Design", J. Cardiovascular Pharmacology, 10 (Suppl. 7)5:54-58, 1987.
Plattner et al., "Renin Inhibitors. Dipeptide Analogues", J. Med. Chem. 1988, 31, 2272-2288.

Primary Examiner—Merrell C. Cashion, Jr.
Assistant Examiner—B. Celsa
Attorney, Agent, or Firm—Millen, White, Zelano & Branigan

[57] ABSTRACT

New amino acid derivatives of the formula $$R^1-Z-NR^2-CHR^3-CR^4-(CHR^5)_a-CO-E-Q-Y$$

wherein $R^1$ to $R^5$, a, Z, E, Q and Y have the meanings defined herein, and salts thereof inhibit the activity of human plasma renin.

18 Claims, No Drawings

AMINOACID DERIVATIVES INHIBITING RENIN

SUMMARY OF THE INVENTION

The invention relates to new aminoacid derivatives of the formula I

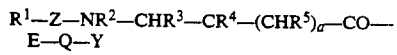

wherein $R^1$ is $R^7$—CO— or $R^7$—CO—CH$_2$—CH($R^8$—C$_p$H$_{2p}$)—C$_r$H$_{2r}$—CO—, Z is 1 to 4 aminoacid radicals linked to one another by a peptide linkage and selected from the group consisting of Abu, Ada, Ala, βAla, Arg, Asn, Asp, Bia, Cal, Dab, Gln, Glu, Gly, His, N(im)-A-His, Hph, Ile, Leu, tert.-Leu, Lys, Mal, Met, αNal, βNal, Nbg, Nle, Orn, Phe, Pia, Pro, Pya, Ser, Thr, Tia, Tic, Trp, Tyr and Val, E is 0 to 2 aminoacid radicals linked to one another by a peptide linkage and selected from the group consisting of Abu, Ala, Cal, Hi, Ile, Leu, Met, Nle, Nva, Phe, Trp, Tyr and Val, Q is O or NR$^6$, Y is —C$_5$H$_{2t}$—R$^{13}$, —C$_t$H$_{2t}$—R$^{14}$ or —C$_w$H$_{2w}$—(CR$^{15}$)$_a$—C$_5$H$_{2t}$—R$^{13}$, $R^2$, $R^5$, $R^6$, $R^9$ and $R^{11}$ are each H or A, $R^3$, $R^8$ and $R^{13}$ are each H, A, Ar, Ar-alkyl, Het or Het-alkyl, or cycloalkyl having 3-7 C atoms, cycloalkylalkyl having 4-11 C atoms, bicycloalkyl or tricycloalkyl having in each case 7-14 C atoms or bicycloalkylalkyl or tricycloalkylalkyl having in each case 8-18 C atoms, each of which is unsubstituted or monosubstituted or polysubstituted by A, AO and/or Hal, $R^4$ and $R^{15}$ are each (H, OH), (H, NH$_2$) or =O, $R^7$ is $R^9R^{10}$N—C$_j$H$_{2j}$—T—C$_k$H$_{2k}$—, $R^{10}R^{11}$N—C$_m$H$_{2m}$—V—C$_n$H$_{2n}$— or $R^{12}$—C$_m$H$_{2m}$—L—C$_n$H$_{2n}$—, $R^{10}$ is H, A or Ac, $R^{12}$ is pyridyl, pyridazinyl, pyrimidinyl, pyrazinyl, pyrrolidinyl, piperidinyl, hexahydroazepinyl, morphiolinyl or thiomorpholinyl, $R^{14}$ is —SO$_3$H, —SO$_2$NH$_2$, —SO$_2$NHA, —SO$_2$NA$_2$, —NH$_2$, —NHA, —NA$_2$, —NA$_3$⊕An⊖, —NH—C(=NH)—NH$_2$, —NH—C(=NH)—NHCN, —NH—CO—NH$_2$, —NH—CO—NHA, —NH—CO—NA$_2$, —NH—CS—NH$_2$, —NH—CS—NHA or —NH—CS—NA$_2$, L is 1,4-piperidinylene or 1,4-piperazinylene, T is O, S, NH or NA, V is phenylene or cyclohexylene, $R^9R^{10}$N, $R^{10}R^{11}$N and/or $R^{12}$ can also be a pyrrolidino, piperidino, hexahydroazepino, morpholino or piperazino group which is unsubstituted or substituted by A, OH, NH$_2$, NHA, NA$_2$, NHAc, NH—CO—C$_x$H$_{2x}$—O—R$^{16}$, NH—CO—O—C$_x$H$_{2x}$—O—R$^{16}$, hydroxyalkyl, COOH, COOA, CONH$_2$, aminoalkyl, NAN-alkyl, A$_2$N-alkyl, A$_3$N⁻alkyl An⊖, guanidinyl or guanidinyl-alkyl, $R^{16}$ is A or Ar-alkyl, a and s are each 1 or 2, j and k are each 1, 2, 3, 4, 5 or 6, m, n, p, r, t, w and x are each 0, 1, 2, 3, 4, 5, 6, 7, 8, 9 or 10, Ar is phenyl which is unsubstituted or monosubstituted or polysubstituted by A, OA, Hal, CF$_3$, OH, NO$_2$, hydroxyalkyl, NH$_2$, NHA, NA$_2$, NHAc, SA, SO—A, SO$_2$—A, SO$_2$NH$_2$, SO$_2$NHA, COOH, COOA, CONH$_2$, CN, aminoalkyl, HAN-alkyl, A$_2$N-alkyl, A$_3$N⊕alkyl AN⊖ and/or guanidinylalkyl, or is unsubstituted naphthyl, Het is a saturated or unsaturated 5-membered or 6-membered heterocyclic radical which has 1-4 N, O and/or S atoms, which can be fused with a benzene ring and/or can be monosubstituted or polysubstituted by A, OA, Hal, CF$_3$, OH, NO$_2$, carbonyl oxygen, NH$_2$, NHA, NA$_2$, NHAc, SA, SO—A, SO$_2$—A, SO$_2$NH$_2$, SO$_2$NHA, COOH, COOA, CONH$_2$, CN, NH—SO$_2$—A, Ar, Ar-alkyl, Ar-alkenyl, hydroxyalkyl, aminoalkyl, HAN-alkyl and/or A$_2$N-alkyl and/or the N and/or S heteroatoms thereof can also be oxidized, Hal is F, Cl, Br or I, Ac is A—CO—, Ar—CO—, Ar-alkyl—CO—, A—O—CO—, Ar-alkyl—O—CO— or A—NH—CO—, An⊖ is an anion which can also be absent if instead a carboxyl group contained in the compound of the formula I is present in form of a carboxylate aninon, -alkyl- is an alkylene group having 1-8 C atoms and A is alkyl having 1-8 C atoms, and wherein, furthermore, one or more —NA—CO— groups can also take the place of one or more —NH—CO— groups, and also salts thereof, including the quaternary ammonium salts.

In the foregoing, selection of variables defined together is made independently.

Similar compounds are known from EP-A 249,096.

The invention was based on the object of finding new compounds having valuable properties, in particular new compounds which can be used for the preparation of medicaments.

Upon further study of the specification and appended claims, further object and advantages of this invention will become apparent to those skilled in the art.

It has been found that the compounds of the formula I and their salts possess very valuable properties. Above all they inhibit the activity of human plasma renin. This action can be demonstrated, for example, by the method of F. Fyhrquist et al., Clin.Chem. 22, 250–256 (1976). It is remarkable that these compounds are very specific inhibitors of renin; as a rule concentrations about 100 to 1000 times as high of these compounds are required for the inhibition of other aspartyl proteinases (for example pepsin and cathepsin D) as are required for renin inhibition. The effects of the compounds on the blood pressure and/or on the heart rate and the inhibition of renin activity in blood plasma can also be determined on conscious monkeys, for example female monkeys (*Macaca fascicularis*); moreover blood pressure and heart rate can be measured in a manner similar to the method of M. J. Wood et al., J. Hypertension 4, 251–254 (1985). In order to stimulate the renin activity, the animals are preferably pretreated with a saluretic. Blood samples for determining the plasma renin activity can be obtained by puncture of the femoral vein.

The compounds can be employed as active compounds for medicaments in human and veterinary medicine, particularly for the prophylaxis and treatment of cardiac, circulatory and vascular diseases, aboe all hypertension, cardiac insufficiency and hyperaldosteronism. In addition the compounds can be used for diagnostic purposes, in order to determine, in the case of patients having hypertension or hyperaldosteronism, the possible contribution made by renin activity towards maintaining the pathological state. Such diagnostic tests can be carried out by methods similar to that indicated in EP-A 77,028.

The abbreviations of aminoacid radicals listed above and below stand for the radicals —NR'—R"—CO—, as a rule —NH—CHR—CO— (wherein R, R' and R" have the specific meaning known for each aminoacid), of the following aminoacids:

Abu: 2-aminobutyric acid
Ada: 3-(1-adamantyl)-alanine
AHCH: 4S-amino-3S-hydroxy-6-cyclohexylhexanoic acid
AHCP: 4S-amino-3S-hydroxy-5-cyclohexylpentanoic acid
AHPP: 4S-amino-3S-hydroxy-5-phenylpentanoic acid
Ala: alanine
βAla: βalanine
Arg: arginine
Asn: asparagine
Asp: aspartic acid
Bia: 3-(2-benzimidazolyl)alanine
Cal: 3-cyclohexylalanine
Dab: 2,4-diaminobutyric acid
DACH: 3S,4S-diamino-6-cyclohexylhexanoic acid
DACP: 3S,4S-diamino-5-cyclohexylpentanoic acid
DAMH: 3S,4S-diamino-6-methylheptanoic acid
DAPP: 3S,4S-diamino-5-phenylpentanoic acid
Gln: glutamine
Glu: glutamic acid
Gly: glycine
His: histidine
N(im)-A-His: histidine which is substituted by A in the 1-position or 3-position of the imidazole ring
Hph: homophenylalanine (2-amino-4-phenylbutyric acid)
Ile: isoleucine
Leu: leucine
tert.-Leu: tert.-leucine
Lys: lysine
Mal: 3-(p-methoxyphenyl)alanine
Met: methionine
αNal: 3-(α-naphthyl)alanine
βNal: 3-(β-naphthyl)alanine
Nbg: 2-norbornyl glycine
Nle: norleucine
N-Me-His: N-methylhistidine
N-Me-Phe: N-methylphenylalanine
Orn: ornithine
Phe: phenylalanine
Pia: 3-(piperidyl)alanine [e.g., 2-Pia=3-(2-piperidyl)alanine]
Pro: proline
Pya: 3-(pyridyl)alanine [e.g., 3-Pya=3-(3-pyridyl)alanine]
Ser: serine
Sta: statine
Thr: threonine
Tia: 3-(thienyl)alanine [e.g., 2-Tia=3-(2-thienyl)alanine]
Tic: 1,2,3,4-tetrahydroisoquinoline-1-carboxylic acid
Trp: tryptophan
Tyr: tyrosine
Val: valine.

There are also the following abbreviations:
BOC: tert.-butoxycarbonyl
BOM: benzyloxymethyl
imi-BOM: benzyloxymethyl in the 1-position of the imidazole ring
CBZ: benzyloxycarbonyl
DCCI: dicyclohexylcarbodiimide
DMF: dimethylformamide
DNP: 2,4-dinitrophenyl
imi-DNP: 2,4-dinitrophenyl in the 1-position of the imidazole ring
ETOC: ethoxycarbonyl
FMOC: 9-fluorenylmethoxycarbonyl
HOBt: 1-hydroxybenzotriazole
IPOC: isopropoxycarbonyl
POA: phenoxyacetyl
THF: tetrahydrofuran.

Insofar as the aminoacids mentioned above can occur in several enantiomeric forms, all these forms and also mixtures thereof (for example the DL forms) are included in the preceding and following text, for example as a constituent of the compounds of the formula I. The L forms are preferred. Insofar as individual compounds are listed below, the abbreviations of these aminoacids related in each case to the L form, unless anything to the contrary is expressly indicated.

The invention also relates to a process for the preparation of an aminoacid derivative of the formula I and salts thereof, characterized in that it is liberated from one of its functional derivatives by treatment with a solvolyzing or hydrogenolyzing agent, or a carboxylic acid of the formula II $$R^1-G^1-OH \qquad \text{II}$$

wherein
G$^1$
 (a) is absent,
 (b) is Z$^1$,
 (c) is Z,
 (d) is Z—W—,
 (e) is Z—W—E$^1$—,
 (f) is Z—W—E— and
W is —NR$^2$—CHR$^3$—CR$^4$—(CHR$^5$)$_a$—CO— is one of its reactive derivatives is reacted with an amino compound of the formula III $$H-G^2 \qquad \text{III}$$

wherein
G$^2$
 (a) is —Z—W—E—Q—Y,
 (b) is —Z$^2$—W—E—Q—Y,
 (c) is —W—E—Q—Y,
 (d) is —E—Q—Y,
 (e) is —E$^2$—Q—Y,
 (f) is —NR$^6$—Y and
Z$^1$+Z$^2$ together are Z, or a compound of the formula IV $$R^{17}-H \qquad \text{IV}$$

wherein
R$^{17}$
 (a) is R$^9$R$^{10}$N—,
 (b) is R$^{10}$R$^{11}$N—,
 (c) is R$^9$R$^{10}$N—C$_j$H$_{2j}$—T—, or
 (d) is R$^{12}$C$_m$H$_{2m}$—L—, or one of its reactive derivatives is reacted with a compound of the formula V $$R^{18}-CO-[CH_2-CH(R^8-C_pH_{2p})-C_rH_{2r}-CO]_y-Z-W-E-Q-Y \qquad \text{V}$$

wherein
R$^{18}$ (a) is X—$C_jH_{2j}$—T—$C_kH_{2k}$,
(b) is X—$C_mH_{2m}$—V—$C_nH_{2n}$—,
(c) is X—$C_kH_{2k}$—,
(d) is X—$C_nH_{2n}$—, X is Hal or a reactive esterified OH group and y is 0 or 1, and, if appropriate, a functionally modified amino and/or hydroxyl group in a compound of the formula I is liberated by treatment with solvolyzing or hydrogenolyzing agents and/or, in order to prepare a compound of the formula I, $R^4$=(H, OH) or (H, $NH_2$), an aminoketo acid derivative of the formula I, $R^4$=O, is reduced or reductively aminated and/or a compound of the formula I is converted into one of its salts by treatment with an acid, a base or a quaternizing agent.

In the preceding and following text the radicals or parameters $R^1$ to $R^{18}$, Z, E, Q, L, T, V, a, j, k, m, n, p, r, s, t, w, x, Ar, Het, Hal, Ac, An, A, $G^1$, $G^2$, W, $Z^1$, $Z^2$, X and y have the meanings indicated in the formulae I, II, III, IV and V, unless anything to the contrary is expressly indicated.

In the above formulae A has 1–8, preferably 1, 2, 3 or 4, C atoms. A is preferably methyl and also ethyl, propyl, isopropyl, butyl, isobutyl, sec.-butyl, or tert.-butyl, and also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1-ethylbutyl, 2-ethylbutyl, 1-ethyl-1-methylpropyl, 1-ethyl-2-methylpropyl, 1,1,2-trimethylpropyl, 1,2,2-trimethylpropyl, heptyl or octyl.

Typically, all alkyl portions mentioned above have up to 8 carbon atoms, including the alkenyl and alkylene portions of Ar-alkenyl, Ar-alkyl, Het-alkyl, hydroxyalkyl, aminoalkyl, HAN-alkyl, $A_2$N-alkyl, $A_3N^\oplus$ alkyl $An^\ominus$, guanidinylalkyl, Ar-alkyl—CO and Ar-alkyl-O—CO.

Cycloalkyl is preferably cyclopropyl, cyclobutyl, cyclopentyl, cyclohexyl, or cycloheptyl, but also, for example, 1-, 2- or 3-methylcyclopentyl or 1-, 2-, 3- or 4-methylcyclohexyl.

Accordingly, cycloalkylalkyl is preferably cyclopropylmethyl, 2-cyclopropylethyl, cyclobutylmethyl, 2-cyclobutylethyl, cyclopentylmethyl, 2-cyclopentylethyl, cyclohexylmethyl, 2-cyclohexylethyl, but also, for example, 1-, 2- or 3-methylcyclopentylmethyl or 1-, 2-, 3- or 4-methylcyclohexylmethyl.

Bicycloalkyl is preferably 1-decalyl, 2-decalyl, 2-bicyclo[2.2.1]heptyl or 6,6-dimethyl-2-bicyclo[3.1.1.]hetpyl.

Tricycloalkyl is preferably 1-adamantyl.

Hal is preferably F, Cl or Br, but also I.

Ac is preferably A—CO—, such as acetyl, propionyl or butyryl, Ar—CO—, such as benzoyl, o-, m- or p-methoxybenzoyl or 3,4-dimethoxybenzoyl, or A—N-H—CO—, such as N-methylcarbamoyl or N-ethylcarbamoyl.

Ar is preferably phenyl, and also preferably o-, m- or p-tolyl, o-, m- or p-ethylphenyl, o-, m-, or p-methoxyphenyl, o-, m- or p-fluorophenyl, o-, m- or p-chlorophenyl, o-, m-, or p-bromophenyl, o-, m-, or p-iodophenyl, o-, m-, or p-trifluoromethylphehyl, o-, m-, or p-hydroxyphenyl, o-, m- or p-sulfamoylphenyl, 2,3-, 2,4-, 2,5-, 2,6-, 3,4- or 3,5-dimethoxyphenyl, 3,4,5-trimethoxyphenyl, o-, m- or p-aminophenyl, o-, m-, or p-aminomethylphenyl, o-, m- or p-dimethylaminomethylphenyl, o-, m- or p-guanidinomethylphenyl, 1- or 2-naphthyl.

Accordingly, Ar-alkyl is preferably benzyl, 1-phenylethyl, 2-phenylethyl, o-, m- or p-methylbenzyl, 1-o-, -m- or -p-tolylethyl, 2-o-, -m- or -p-tolylethyl, o-, m- or p-ethylbenzyl, 1-o-, -m- or -p-ethylphenylethyl, 2-o-, -m- or -p-ethylphenylethyl, o-, m- or p-methoxybenzyl, 1-o-, -m- or -p-methoxyphenylethyl, 2-o-, -m- or -p-methoxyphenylethyl, o-, m- or p-fluorobenzyl, 1-o-, -m- or p-fluorophenylethyl, 2-o-, -m- or -p-fluorophenylethyl, o-, m- or p-chlorobenzyl, 1-o-, -m- or -p-chlorophenylethyl, 2-o-, -m- or -p-chlorophenylethyl, o-, m- or p-bromobenzyl, 1-o-, -m- or -p-bromophenylethyl, 2-o-, -m- or -p-bromophenylethyl, o-, m- or p-iodobenzyl, 1-o-, -m- or -p-iodophenylethyl, 2-o-, -m- or -p-iodophenylethyl, o-, m- or p-trifluoromethylbenzyl, o-, m- or p-hydroxybenzyl 2,3-, 2,4-, 2,5-, 2,6-, 3,4- or 3,5-dimethoxybenzyl, 3,4,5-trimethoxybenzyl, o-, m- or p-aminobenzyl, o-, m- or p-aminomethylbenzyl, o-, m- or p-dimethylaminomethylbenzyl, o-, m- or p-guanidinomethylbenzyl, 1- or 2-naphthylmethyl.

Het is preferably 2-furyl, 3-furyl, 2-thienyl, 3-thienyl, 1-, 2- or 3-pyrrolyl, 1-, 2-, 4- or 5-imidazolyl, 1-, 3-, 4- or 5-pyrazolyl, 2-, 4-, or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, and also preferably 1,2,3-triazol-1-, -4-, or -5-yl, 1,2,4-triazol-1-, -3- or -5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl, 1,3,4-thiadiazol-5-yl, 1,2,4-thiadiazol-3-yl, 1,2,4-thiadiazol-5-yl, 2,1,5-thiadiazol-3-yl, 2,1,5-thiadiazol-4-yl, 2-, 3-, 4-, 5- or 6-2H-thiopyranyl, 2-, 3- or 4-4H-thiopyranyl, 3-pyridazinyl, 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 3-, 4-, 5-, 6- or 7-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7 or 8-quinolyl, 1-, 3-, 4-, 5-, 6-, 7-, or 8-isoquinolyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolyl, 2-, 4-, 5-, 6-, 7- or 8-quinazolyl. The heterocyclic radicals can also be partly or completely hydrogenated. Het can thus, for example, also be 2,3-dihydro-2-, -3-, -4- or -5-furyl, 2,5-dihydro-2-, -3-, -4- or -5-furyl, tetrahydro-2- or -3-furyl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The heterocyclic radicals can also be substituted as indicated. Het can preferably also be, for example: 2-amino-4-thiazolyl, 4-carboxy-2-thiazolyl, 4-carbamoyl-2-thiazolyl, 4-(2-aminoethyl)-2-thiazolyl, 4-amino-2-methyl-5-pyrimidinyl, 2-amino-5,6-dimethyl-3-pyrazinyl, 4-carbamoylpiperidino, and also, for example, 3-, 4- or 5-methyl-2-furyl, 2-, 4- or 5-methyl-3-furyl, 2,4-dimethyl-3-furyl, 5-nitro-2-furyl, 5-styryl-2-furyl, 3-, 4- or 5-methyl-2-thienyl, 2-, 4- or 5-methyl-3-thienyl, 3- methyl-5-tert.butyl-2-thienyl, 5-chloro-2-thienyl, 5-phenyl-2-thienyl, 5-phenyl-3-thienyl, 1-, 3-, 4- or 5-methyl-2-pyrrolyl, 1-methyl-4-nitro-2-pyrrolyl, 1-methyl-5-nitro-2-pyrrolyl, 3,5-dimethyl-4-ethyl-2-pyrrolyl, 4-methyl-5-pyrazolyl, 5-methyl-3-isoxazolyl, 3,4-dimethyl-5-isoxazolyl, 4-methyl-2-thiazolyl, 5-methyl-2-thiazolyl, 2-methyl-4-thiazolyl, 5-methyl-4-thiazolyl, 2-methyl-5-thiazolyl, 4-methyl-5-thiazolyl, 2,4-dimethyl-5-thiazolyl, 3-, 4-, 5-, or 6-methyl-2-pyridyl, 2-, 4-, 5- or 6-methyl-3-pyridyl, 2-methyl-4-pyridyl, 3-methyl-4-pyridyl, 3-, 4- 5- or 6-chloro-2-pyridyl, 2-, 4-, 5- or 6-chloro-3-pyridyl, 2-chloro-4-pyridyl, 3-chloro-4-pyridyl, 2,6-dichloropyridyl, 2-hydroxy-3-, -4-, -5-, or -6-pyridyl (=1H-2-pyridon-3-, -4-, -5- or -6-yl), 5-phenyl-1H-2-pyridon-3-yl, 5-p-methoxyphenyl-1H-2-pyridon-3-yl, 2-methyl-3-yl, 2-methyl-3-hydroxy-4-hydroxymethyl-5-pyridyl, 2-hydroxy-4-amino-6-methyl-3-pyridyl, 3-N'-methylureido-1H-4-pyridon-5-yl, 4-methyl-2-pyrimidinyl, 4,6-dimethyl-2-pyrimidinyl, 2-, 5- or 6-methyl-4-pyrimidinyl, 2,6-dimethyl-4-pyrimidinyl, 2,6-dihydroxy-4-pyrimidinyl, 5-chloro-2-methyl-4-pyrimidinyl, 3-methyl-2-benzofuryl, 2-ethyl-3-benzofuryl, 7-methyl-2-benzothienyl, 1-, 2-, 4-, 5-, 6- or 7-methyl-3-indolyl, 1-methyl-5-benzimidazolyl, 1-methyl-6-benzimidazolyl, 1-ethyl-5-benzimidazolyl, 1-ethyl-6-benzimidazolyl, 3-, 4-, 5-, 6-, 7- or 8-hydroxy-2-quinolyl, 2-oxo-pyrrolidino, 2-oxo-piperidino, 2,5-dioxopyrrolidino, 3-benzyl-2,5-dioxopyrrolidino.

In general, $R^1$ is preferably $R^7$—CO—.

The group Z preferably consists of one or two of the aminoacid radicals indicated; it can, however, also contain three or four amin oacid radicals. Z is preferably Phe-Gly or Phe-$\beta$Ala, and also Gly, $\beta$Ala, Mal, Phe, $\alpha$Nal, $\beta$Nal, Pya, Phe-His, Phe-Pya and also preferably Abu, Ala, Bia, Cal, His, Hph, Ile, Leu, tert.-Leu, Met, Nle, Pia, Ser, Thr, Tia, Trp, Tyr, Val, Mal-Gly, $\alpha$Nal-Gly, $\beta$Nal-Gly, Phe-Abu, Phe-Ada, Phe-Ala, Phe-Arg, Phe-Asn, Phe-Asp, Phe-Bia, Phe-Cal, Phe-Dab, Phe-Gln, Phe-Glu, Phe-N(im)-Me-His, Phe-Hph, Phe-Ile, Phe-Leu, Phe-tert.-Leu, Phe-Lys, Phe-Mal, Phe-Met, Phe-$\alpha$Nal, Phe-$\beta$Nal, Phe-Nbg, Phe-Nle, Phe-Orn, Phe-Phe, Phe-Pia, Phe-Pro, Phe-Ser, Phe-Thr, Phe-Tia, Phe-Tic, Phe-Trp, Phe-Tyr, Pro-Phe-His or His-Pro-Phe-His.

If $R^1$ is an $R^7$—CO—CH$_2$—CH($R^8$—C$_p$H$_{2p}$—CO group, Z is preferably Gly or $\beta$Ala.

$R^2$, $R^5$, $R^6$, $R^9$ and $R^{11}$ are each preferably H, and also preferably methyl; $R^5$ is also preferably isopropyl or isobutyl. $R^9R^{10}N$ and $R^{10}R^{11}N$ are also preferably pyrrolidino, piperidino, morpholino, aminopiperidino, such as 4-aminopiperidino, alkylaminopiperidino such as 4-methyl-aminopiperidino, or dialkylaminopiperidino, such as 4-dimethylaminopiperidino.

$R^3$ is preferably cycloalkylalkyl, especially cyclohexylmethyl, and also preferably alkyl, especially isobutyl; Ar-alkyl, in particular benzyl; or cycloalkyl, especially cyclohexyl.

$R^4$ and $R^5$ are preferably (H, OH).

$R^7$ is preferably $R^{10}R^{11}N$—C$_m$H$_{2m}$—V—C$_n$H$_{2n}$—.

$R^8$ is preferably Ar, preferably specifically phenyl, o-, m- or, in particular p-hydroxyphenyl, o-, m- or, in particular, p-methoxyphenyl, 1-naphthyl or 2-naphthyl.

$R^{10}$ is preferably H, methyl, acetyl, BOC or CBZ.

$R^{12}$ is preferably 2-, 3- or 4-pyridyl, 2-, 4- or 5-pyrimidinyl, 1-(=piperidino), 2-, 3- or 4-piperidinyl, but also 3-pyridazinyl, 4-pyridazinyl, pyrazinyl, 1-(=pyrrolidino), 2- or 3-pyrrolidinyl, 1-(=hexahydroazepino), 2-, 3- or 4-hexahydroazepinyl, 1-(=morpholino), 2- or 3-morpholinyl, or 1-(=thiomorpholino), 2- or 3-thiomorpholinyl.

$R^{16}$ is preferably A having 1–4 C atoms, especially isopropyl or tert.-butyl; or is Ar-alkyl, especially benzyl.

L is preferably 1,4-piperazinylene, but also 1,4-piperidinylidene.

T is preferably O, S or NH.

V is preferably 1,4-cyclohexylene, also preferably 1,4-phenylene, but also 1,2-cyclohexylene, 1,3-cyclohexylene, 1,2-phenylene or 1,3-phenylene.

The parameters a and s are in each case preferably 1.

The parameter j is preferably 2 or 3; k is preferably 1, but also 2. The parameters m and n are preferably 0, but also 1, 2, 3, 4 or 5; p is preferably 1; r is preferably 1 or 0. The groups $C_jH_{2j}$, $C_kH_{2k}$, $C_mH_{2m}$, $C_nH_{2n}$, $C_pH_{2p}$ are preferably linear and are thus preferably —(CH$_2$)$_j$—, —(CH$_2$)$_k$—, —(CH$_2$)$_m$—, —(CH$_2$)$_n$—, —(CH$_2$)$_p$—, or —(CH$_2$)$_r$—. The groups $C_tH_{2t}$ and $C_wH_{2w}$ are each preferably —CH$_2$—, —(CH$_2$)$_2$—, —CH(CH$_3$)— —CH(isobutyl)— or —CH(sec.-butyl)—; the groups $C_mH_{2m}$, $C_nH_{2n}$ and/or $C_tH_{2t}$ can also preferably be absent (m, and/or t=0). The parameter x is preferably 1 and also preferably 0 or 2.

Accordingly, the group $R^1$ is, specifically, preferably dialkylaminoalkoxyalkyl, such as 2-dimethylaminoethoxymethyl or 2-diethylaminoethoxymethyl; pyrrolidinoalkoxyalkyl, such as 2-pyrrolidinoethoxymethyl; piperidinoalkoxyalkyl, such as 2-piperidinoethoxymethyl; morpholinoalkoyalkyl, such as 2-morpholinoethoxymethyl; dialkylaminothioalkyl, such as 2-dimethylaminoethylthiomethyl, 2-(2-dimethylaminoethylthio)ethyl, 3-(2-dimethylaminoethylthio)-propyl, or 2-diethylaminoethylthiomethyl; pyrrolidinoalkylthioalkyl, such as 2-yrrolidinoethylthiomethyl; piperidinoalkylthioalkyl, such as 2-piperidinoethylthiomethyl; morpholinoalkylthioalkyl, such as 2-morpholinoethylthiomethyl; dialkylaminoalkylaminoalkyl, such as 2-dimethylaminoethylaminomethyl or 2-diethylaminoethylaminomethyl; pyrrolidinoalkylaminoalkyl, such as 2-pyrrolidinoethylaminomethyl; piperidinoalkylaminoalkyl, such as 2-iperidinoethylaminomethyl; morpholinoalkylaminoalkyl, such as 2-morpholinoethylaminoethyl; 4-aminocyclohexyl; 4-alkylaminocyclohexyl, such as 4-methylaminocyclohexyl or 4-ethylaminocyclohexyl; 4-dialkylaminocyclohexyl, such as 4-dimethylaminocyclohexyl or 4-diethylaminocyclohexyl; 4-pyrrolidinocyclohexyl; 4-piperidinocyclohexyl; 4-hexahydroazepinocyclohexyl; 4-morpholinocyclohexyl; 4-aminomethylcyclohexyl; 4-alkylaminomethylcyclohexyl, such as 4-methylaminomethylcyclohexyl or 4-ethylaminomethylcyclohexyl; 4-dialkylaminomethylcyclohexyl, such as 4-dimethylaminomethylcyclohexyl or 4-diethylaminomethylcyclohexyl; 4-pyrrolidinomethylcyclohexyl; 4-piperidinomethylcyclohexyl; 4-hexahydroazepinomethylcyclohexyl; 4-morpholinomethylcyclohexyl; 4-aminocyclohexylmethyl; 4-alkylaminocyclohexylmethyl, such as 4-methylaminocyclohexylmethyl or 4-ethylaminocyclohexylmethyl; 4-dialkylaminocyclohexylmethyl, such as 4-dimethylaminocyclohexylmethyl or 4-diethylaminocyclohexylmethyl; 4-pyrrolidinocyclohexylmethyl; 4-piperidinocyclohexylmethyl; 4-hexahydroazepinocyclohexylmethyl; 4-morpholinocyclohexylmethyl; 4-aminophenyl; 4-alkylaminophenyl, such as 4-methylaminophenyl, 4-ethylaminophenyl; 4-dialkylaminophenyl, such as 4-dimethylaminophenyl, 4-diethylaminophenyl; 4-pyrrolidinophenyl; 4-piperidinophenyl; 4-hexahydroazepinophenyl; 4-morphilinophenyl; 4-aminobenzyl; 4-alkylaminobenzyl, such as 4-methylaminobenzyl, 4-ethylaminobenzyl; 4-dialkylaminobenzyl, such as 4-dimethylaminobenzyl, 4-diethylaminobenzyl; 4-pyrrolidinobenzyl; 4-piperidinobenzyl; 4-hexahydroazepinobenzyl; or 4-morpholinobenzyl.

4-(2-pyridyl)-piperidino, 4-(3-pyridyl)-piperidino, or 4-(4-pyridyl)-piperidino; 4-(3-pyridazinyl)piperidino or 4-(4-pyridazinyl)-piperidino; 4-(2-pyrimidinyl)-piperidino, 4-(4-pyrimidinyl)-piperidino, or 4-(5-pyrimidinyl)-piperidino; 4-pyrazinylpiperidino; 4-pyrrolidinopiperidino 4-(2-pyrrolidinyl)-piperidino, 4-(3-pyrrolidinyl)-piperidino, 4-piperidinopiperidino, 4-(2-piperidinyl)-piperidino, 4-(3-piperidinyl)-piperidino, 4-(4-piperidinyl)-piperidino, 4-hexahydroazepinopiperidino, 4-(2-hexyhydroazepinyl)-piperidino, 4-(3-hexyhydroazepinyl)-piperidino, 4-(4-hexahydroazepinyl)piperidino, 4-morpholinopiperidino, 4-(2-morpholinyl)-piperidino, 4-(3-morpholinyl)-piperidino, 4-thiomorpholinopiperidino, 4-(2-thiomorpholinyl)-piperidino, 4-(3-thiomorpholinyl)-piperidino, 4-(2-pyridyl)-piperidinoalkyl, 4-(3-pyridnyl)-piperidinoalkyl or 4-(4-pyridyl)-piperidinoalkyl, such as 4-(2-pyridyl)-piperidinomethyl, 4-(4-pyridyl)-piperidinomethyl, 4-(4-pyridyl)-piperidinomethyl, 2-[4-(2-pyridyl)-pipeidinol]-ethyl, 2-[4-(3-pyridyl)-piperidino]-ethyl or 2-[4-(4-pyridyl)-piperidinol-ethyl; 4-(2-pyridyl)-piperazino, 4-(3-pyridyl)-piperazino, or 4(4-pyridyl)-piperazino; 4-(3-pyridazinyl)-piperazino or 4-(4-pyridazinyl)-piperazino; 4-(2-pyrimidinyl)piperazino, 4-(4-pyrimidinyl)-piperazino or 4-(5-pyrimidinyl)-piperazino; 4-pyrazinyl-piperazino; 4-pyrrolidinopiperazino, 4-(2-pyrrolidinyl)-piperazino or 4-(3-pyrrolidinyl)-piperazino, 4-piperidinopiperazino, 4-(2-piperidinyl)-piperazino, 4-(3-piperidinyl)-piperazino or 4-(4-piperidinyl)-piperazino; 4-hexyhydroazepinopiperazino, 4-(2-hexahydroazepinyl)-piperazino, 4-(3-hexahydroazepinyl)-piperazino or 4-(4-hexahydroazepinyl)-piperazino, 4-morpholinopiperazino, 4-(2-morpholinyl)piperazino or 4-(3-morpholinyl)piperazino, 4-thiomorpholinopiperazino, 4-(2-thiomorpholinyl)-piperazino or 4-(3-thiomorpholinyl)-piperazino, 4-(2-pyridyl)-piperazinoalkyl, 4-(3-pyridyl)-piperazinoalkyl or 4-(4-pyridyl)piperazinoalkyl, such as 4-(2-pyridyl)-piperazinomethyl, 4-(3-pyridyl)-piperazinomethyl, 4-(4-pyridyl)-piperazinomethyl, 2-[4-(2-pyridyl)-piperazino]-ethyl, 2-[4-(3-pyridyl)-piperazino]-ethyl or 2-[4-(4-pyridyl)-piperazino]-ethyl; 4-(3-pyridazinyl)piperazinoalkyl or 4-(4-pyridazinyl)-pyridazinyl)-piperazinoalkyl, such as 4-(3-pyridazinyl)-piperazinomethyl, 4-(4-pyridazinyl)-piperazinomethyl, pyridazinyl)-piperazino]-ethyl; 4-(2-pyrimidinyl)-ppierazinoalkyl, 4-(4-pyrimidinyl)-piperazinoalkyl or 4-(5-jpyrimidinyl)-piperazinoalkyl, such as 4-(2-pyrimidinyl)piperazinomethyl, 4-(4-pyrimidinyl)-piperazinomethyl, 4-(5-pyrimidinyl)-piperazinomethy, 2-[4-(2-pyrimidinyl)piperazino]-ethyl, 2-[4-(4-pyrimidinyl)-piperazino]ethyl, 2-[4-(5-pyrimidinyl)-piperazino]-ethyl, 3-[4-(2-pyrimidinyl)-piperazino]-propyl, 4-[4-(4-pyrimidinyl)piperazino]-propyl, 3-[4-(5-pyrimidinyl)-piperazino]propyl, 4-[4-(2-pyrimidinyl)-piperazino]-butyl, 4-[4-(4-pyrimidinyl)-piperazino-]-butyl, 4-[4-(5-pyrimidinyl)piperazino]-butyl, 5-[4-(2-pyrimidinyl)-piperazino]pentyl, 5-[4-(4-pyrimidinyl)-piperazino]-pentyl or 5-[4-(5-pyrimidinyl)-piperazino]-pentyl; or 4-pyrazinylpiperazino alkyl, such as 4-pyrazinylpiperazinomethyl or 2-(4-pyrazinylpiperazino)-ethyl.

E is preferably one of the amino acid radicals mentioned, in particular Ile or Leu; E is also preferably absent or is preferably Abu, Cal, Met, Nle, Nva, Phe or Val.

Q is preferably $NR^6$, preferably NH or $H(CH_3)$.

Y is preferably $—C_rH_{2r}—R^{13}$ or $C_rH_{2r}—R^{14}$, in particular $—CH_2R^{13}$, $—CH_2R^{14}$ or $—CH_2CH_2R^{14}$. In this regard $R^{13}$ is preferably H, A, Ar or Het, and, specially, is preferably H, alkyl having 3-5 C atoms, phenyl, o-, m- or p-aminomethylphenyl, o-, m- or p-guanidinomethylphenyl, o-, m- or p-dialkylaminomethylphenyl, such as o-, m- or p-dimethylaminomethylphenyl, 2-, 3- or 4-pyridyl, 2-hydroxy-4,6-dimethyl-3-pyridyl, 4-amino-2-methyl-5-pyrimidinyl or 2-amino-5,6-dimethyl-3-pyrazinyl. $R^{14}$ is preferably $—SO_3H$, $—SO_2NH_2$, $—NA_2$, $—NA_3^\ominus An^\ominus$, $—NH—C(=NH)—NH_2$, $—NH—CO—NHA$ or $—NH—CS—NHA$, wherein A is preferably $CH_3$.

The cyclic groups, especially cycloalkyl and phenyl groups, mentioned above are preferably unsubstituted or preferably carry 1 to 3, especially 1 or 2, substituents.

The group W possesses at least one chiral center. Further chiral centers can be present in the group $R^1$, Z, E, Q and Y. The compounds of the formula I can therefore exist in various - optically inactive or optically active - forms. The formula I embraces all these forms. If W is $—NH—CHR^3—CR^4—CH_2—CO—$ in which $R^4—(H, OH)$ or $(H, NH_2)$, the 3S-hydroxy-4S-amino enantiomers or 3S,4S-diamino enantiomers are preferred. The abbreviations AHCP, AHCH, Sta, AHPP, DACP, DACH, DAMH and DAPP relate in each case to the 3S,4S forms.

Accordingly, the invention relates particularly to compounds of the formula I in which at least one of the radicals mentioned has one of the preferred meanings indicated above. Some preferred groups of compounds can be expressed by means of the following partial formulas Ia to Ik:

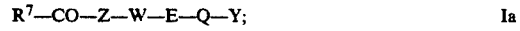
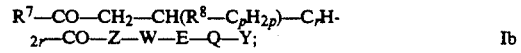
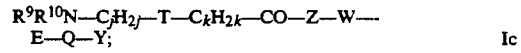
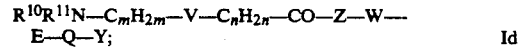
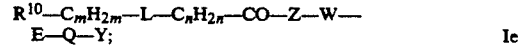
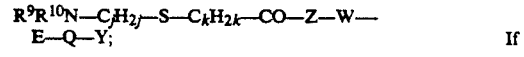
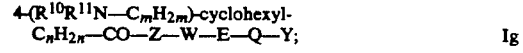
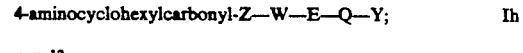
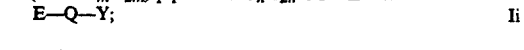
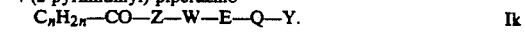

Compounds of the following partial formulae are particularly preferred:

(a) Iaa and Ica to Ika which correspond to the formulae Ia and Ic to Ik, but wherein additionally Z is Phe-βAla, Phe-Gly or Phe-His, and also Iba which corresponds to the formula Ib, but wherein additionally Z is Gly or βAla;

(b) Iab to Ikb and also Iaah to Ikab which correspond to the formulae Ia to Ik and also Iaa to Ika, but wherein additionally W is AHCP;

(c) Iac to Ikc, Iaac to Ikac, Iabc to Ikbc and also Iaab to Ikabc which correponds to the formulae Ia to Ik, Iaa to Ika, Iab to Ikb and also Iaab to Ikab, but wherein additionally E is Ile or Leu.

Compounds of the following partial formulae are particularly preferred:

I* and Ia* to Ik* which correspond to the formulae I and Ia to Ik and also compounds which corresponds to the other partial formulae mentioned above, but wherein additionally Q—Y is —NH—A, —NH—CH2—(3-pyridyl), —NH—CH2—(4-amino-2-methyl-5-pyrimidinyl) ("AMPA") or —NH—CH2—(2-amino-5,6-dimethyl-3-pyrazinyl)("ADPA");

I' and Ia' to Ik' which corresponds to the formulae I and Ia to Ik and also compounds which correspond to the other partial formulae mentioned above, but wherein additionally Q-Y is AMPA; and I" and Ia" to Ik" and Iaa" to Ika" which corresponds to the formulae I and Ia to Ik and Iaa to Ika, wherein W—E—Q—Y is AHCP-Ile-AMPA.

The compounds of the formula I and also the starting materials for their preparation are, incidently, prepared by methods known per se, such as are described in the literature (for example in the standard works such as Houben-Weyl, Methoden der organischen Chemie ("Methods of Organic Chemistry"), Georg-Thieme-Verlag, Stuttgart; and also EP-A 45,665, EP-A 77,028, EP-A 77,029, EP-A 81,783, and EP-A 249,096), specifically under reaction conditions which are known per se but are not mentioned here in detail.

If desired, the starting materials can also be formed in situ, in such a way that they are not isolated from the reaction mixture, but are immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which correspond in other respects to the formula I, but, instead of one or more free amino and/or hydroxyl groups, contain corresponding protected amino and/or hydroxyl groups, preferably those which carry an amino protective group instead of an H atom attached to an N atom, for example those which correspond to the formula I, but contain an N(im)-R'-His group (wherein R' is an amino protective group, for example BOM or DNP) instead of an His group, or those of the formula $R^1$—Z—$NR^2$—CH-$R^3$—CH(NHR')—$(CHR^5)_a$—CO—E—Q—Y.

Starting materials which are also preferred are those which, instead of the H atom of a hydroxyl group, carry a hydroxyl protective group, for example those of the formula $R^1$—A—$NR^2$—$CHR^3$—CHOR"—$(CHR^5)_a$—CO—E—Q—Y, wherein R" is a hydroxyl protective group.

It is also possible for several—identical or different—protected amino and/or hydroxyl groups to be present in the molecule of the starting material. If the protective groups present are different from one another, they can in many cases be split off selectively.

The expression "amino protective group" is generally known and relates to groups which are suitable for protecting (blocking) an amino group from chemical reactions, but which can be removed easily after the desired chemical reaction has been carried out at another point in the molecule. Typical examples of such groups are, in particular, unsubstituted or substituted acyl, acyl (for example DNP), aralkoxymethyl (for example BOM) or aralkyl roups (for example benzyl, 4-nitrobenzyl or triphenylmethyl). Since the amino protective groups are removed after the desired reaction (or reaction sequence), their nature and size is in other respects not critical; but those having 1'20, especially 1-8, C atoms are preferred. The expression "acyl group" is to be construed in the widest sense in connection with the present proess. It embraces acyl groups derived from aliphatic, araliphatic, aromatic or heterocyclic carboxylic acids or sulfonic acids and also, in particular, alkoxycarbonyl, aryloxycarbonyl and, above all, aralkoxycarbonyl groups. Examples of acyl groups of this type are alkanoyl, such as acetyl, propionyl or butyryl; aralkanoyl, such as phenylacetyl; aroyl, such as benzoyl or toluyl; aryloxyalkanoyl, such as POA; alkoxycarbonyl, such as methoxycarbonyl, ETOC, 2,2,2-trichloroethoxycarbonyl, IPOC, BOC or 2-iodoethoxycarbonyl; or aralkyloxycarbonyl, such as CBZ, 4-methoxybernzyloxycarbonyl or FMOC. Preferred amino protective groups are BOC, DNP and BOM, and also CBZ, FMOC, benzyl and acetyl.

The expression "hydroxyl protective group" is also generally known and relates to groups which are suitable for protecting a hydroxyl group from chemical reactions, but which can be removed easily after the desired chemical reaction has been carried out at another point in the molecule. Typical examples of such groups are the abovementioned unsubstituted or substituted aryl, aralkyl or acyl groups, and also alkyl groups. The nature and size of the hydroxyl protective groups is not critical, since they are removed again after the desired chemical reaction or reaction sequence; groups having 1-20, in particular 1-10, C atoms are preferred. Examples of hydroxyl protective groups are, inter alia, tert.-butyl, benzyl, p-nitrobenzyl, p-toluenesolfonyl and acetyl, benzyl and acetyl being particularly preferred.

The functional derivatives of compounds of the formula I to be used as starting materials can be prepared in accordance with customary methods of amino acid and peptide synthesis, such as are described, for example, in the standard works and patent applications mentioned, for example also by the Merrifield solid phase method.

The liberation of the compounds of the formula I from their functional derivatives can be carried out—depending on the protective group used—with, for example, strong acids, preferably trifluoroacetic or perchloric acid, but also other strong inorganic acids, such as hydrochloric acid or sulfuric acid, strong organic carboxylic acids, such as trichloroacetic acid, or sulfonic acids, such as benzene sulfonic or p-toluene sulfonic acid. The presence of an additional inert solvent is possible, but not always necessary. Suitable inert solvents are preferably organic acids, for example carboxylic acids, such as acetic acid, ethers, such as THF or dioxane, amides, such as DMF, halogenated hydrocarbons, such as methylene dichloride, and also alcohols, such as methanol, ethanol or isopropanol, and also water. Mixtures of the abovementioned solvents are also suitable. Trifluoroacetic acid is preferably used in perchloric acid is used in the form of a mixture of acetic acid and 70% perchloric acid in the ratio of 9:1. The reaction temperatures for the cleavage are preferably between about 0° and about 50°, it is preferable to carry out the reaction between 15° and 30° (room temperature).

The BOC group can, for example be split off preferably by means of 40% trifluoroacetic acid in methylene dichloride or by means of about 3N to 5N HCl in dioxane at 15°-30°, while the FMOC group can be split off by means of an approximately 5-20% solution of dimethylamine, diethylamine or piperidine in DMF at 15°-30°. The DNP group can, for example, also be split off by means of an approximately 3-10% solution of 2-mercaptoethanol and DMF/water at 15°-30°.

Protective groups which can be removed by hydrogenolysis (for example BOM, CBZ or benzyl) can be split off, for example, by treatment with hydrogen in the presence of a catalyst (for example a noble metal catalyst, such as palladium, preferably on a support, such as charcoal). Suitable solvents in this regard are those indicated above, in particular, for example, alcohols, such as methanol or ethanol, or amides, such as DMF. The hydrogenolysis is carrie out, as a rule, at temperatures between about 0° and 100° and under pressures between about 1 and 200 bar, preferably at 20°-30° and 1-10 bar. Hydrogenolysis of the CBZ group can be carried out easily, for example, over 5-10% Pd-on-C in methanol at 20°-30°.

Compounds of the formula I can also be obtained by direct peptide synthesis from a carboxylic acid (formula II) and an amine component (formula III), the following reactions being possible:

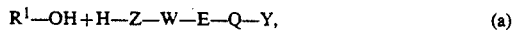   (a)

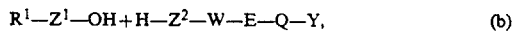   (b)

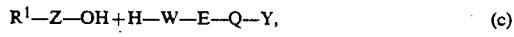   (c)

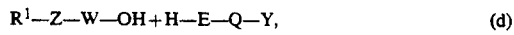   (d)

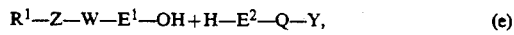   (e)

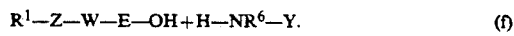   (f)

Thus, in cases (b) and (e) the peptide linkage can be attached within the group Z or E, but only if these groups each contain 2 or more of the amino acid radicals indicated; in this case $Z^1+Z^2$ is Z and $E^1+E^2$ is E. These reactions are preferably carried out by customary methods of peptide synthesis, such as are described, for example, in Houben-Weyl, loc. sit., volume 15/II, pages 1-806 (1974).

The reaction is preferably carried out in the presence of a hydrating agent, for example a carbodiimide, such as DCCI or dimethylaminopropylethylcarbodiimide, and also propanephosphonicanhydride (cf. Angew.-Chem. 92, 129 (1980)), diphenylphosphoryl azide or 2-ethoxy-N-ethoxycarbonyl-1,2,-dihydroquinoline, in an inert solvent, for example a halogenated hydrocarbon, such as methylene dichloride, an ether, such as THF or dioxane, an amide, such as DMF or dimethylacetamide, or a nitrile, such as acetonitrile, at temperatures between about −10 and 40, preferably between 0° and 30°.

Instead of II or III it is also possible to employ suitable reactive derivatives of these compounds in the reaction, for example derivatives in which reactive groups are blocked intermediately by protective groups. The acid derivatives II can be used, for example, in the form of their activated esters, which are preferably formed in situ, for example by the addition for HOBt or N-hydroxysuccinimide.

The starting materials of the formulae II and III are to a large extent known. Insofar as they are not known, they can be prepared by known methods, for example the methods of peptide synthesis indicated above and the detachment of protective groups.

Compounds of the formula I can also be obtained by reacting compounds of the formula IV with compounds of the formula V. In this regard, specifically, the following reactions are possible:

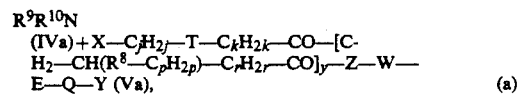   (a)

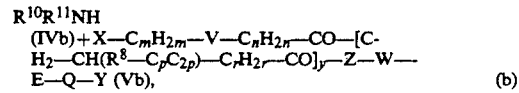   (b)

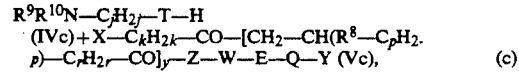   (c)

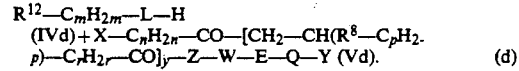   (d)

The starting materials of the formulae IV and V are for the most part known; insofar as they are not known, they can be prepared by methods known per se. The starting materials of the formula V can be obtained, for example, from precursors which correspond to the formula V, but contain a protected OH group instead of X, by liberating the OH group and subsequently reacting it with $SOCl_2$ or $SOBr_2$; the precursors mentioned are, in turn, accessible by methods known per se, for example the methods of peptide synthesis described above.

The reaction of IV with V is preferably carried out in the presence of one of the inert solvents indicated above, for example an alcohol, such as methanol, ethanol or isopropanol, or an ether, such as THF, at temperatures between about 0° and 100°, preferably between 15° and 80°.

If desired, a functionally modified amino and/or hydroxyl group in a compound of the formula I can be liberated by solvolysis or hydrogenolysis by one of the methods described above.

Thus, for example, a compound of the formula I containing an $R^{16}$—O—$C_xH_{2x}$—CO—NH—, an AcNH—, an $ArCH_2$—$SO_3$— or an AOOC— group can be converted into the corresponding compound of the formula I containing, instead, an $H_2N$—, an $HSO_3$— or an HOOC— group, preferably by selective solvolysis in accordance with one of the methods indicated above. AOOC— groups can, for example, be saponified with NaOH or KOH in water/dioxane at temperatures between 0° and 40°, preferably 10° and 30°.

Keto compounds of the formula I ($R^4$=O) can also be reduced to compounds of the formula I ($R^4$=(H, OH)), for example by means of a complex metal hydride, such as $NaBH_4$, which does not simultaneously reduce the peptidecarbonyl groups, in an inert solvent, such as methanol, at temperatures between about −10° and +30°.

Keto compounds of the formula ($R^4$=O) can also be converted into compounds of the formula I ($R^4$=H, $NH_2$) by reductive amination. Reductive amination can be carried out in one or more stages. Thus, for example, it is possible to treat the keto compound with ammonium salts, for example ammonium acetate, and $NaCNBH_3$, preferably in an inert solvent, for example an alcohol, such as methanol, at temperatures between about 0° and 50°, in particular between 15° and 30°. It is also possible first to convert the keto compound into the oxime in a customary manner by means of hydroxylamine and to reduce this oxime to the amine, for example by catalytic hydrogenation over Raney nickel.

A base of the formula I can be converted by means of an acid into the appropriate acid addition salt. Acids suitable for this reaction are those which afford physiologically acceptable salts. Thus, it is possible to use inorganic acids, for example sulfuric acid, nitric acid, hydrogen halide acids, such as hydrochloric acid or hydrobromic acid phosphoric acids, such as orthophosphoric acid, or sulfamic acid, and also organic acids, in particular aliphatic, alicyclic, aralkphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzene sulfonic acid, p-toluenesulfonic acid, naphthalene monosulfonic and naphthalene disulfonic acids or laurylsulfuric acid. Salts with physiologically unacceptable acids, for example picrates, can be used for the isolation and/or purification of the compounds of the formula I.

Bases of the formula I can be converted into the corresponding quaternary ammonium salts by treatment with quaternizing agents, for example alkyl halides, such as methyl chloride, bromide or iodide or ethyl chloride, bromide or idodide, or aralkyl halides, such as benzyl chloride, bromide or iodide. This reaction is preferably carried out in one of the inert solvents indicated, for example an alcohol, such as methanol or ethanol, at temperatures between about 0° and 30°.

The new compounds of the formula I and their physiologically acceptable salts can be used for the preparation of pharmaceutical preparations by bringing them into a suitable dosage form together with at least one excipient or auxiliary and, if desired, together with one or more further active compound(s). The formulations thus obtained can be employed as medicaments in human or veterinary medicine. Suitable excipient substances are organic or inorganic substances which are suitable for enteral administration (for example oral or rectal) or parenteral administration or for administration in the form of an inhalation spray and which do not react with the new compounds, for example water, vegetable oils, benzyl alcohols, polyethylene glycols, glycerol triacetate and other fatty acid glycerides, gelatine, soya lecithin, carbohydrates, such as lactose or starch, magnesium stearate, talc or cellulose. Tablets, coated tablets, capsules, syrups, elixirs or drops are particularly suitable for oral administration; lacquered tablets and capsules with coatings or capsule envelopes resistant to gastric juices are of particular interest. Suppositories are used for rectal administration, while solutions, preferably oily or aqueous solutions, and also suspensions, emulsions or implants are used for parenteral administration. Sprays containing the active compound either dissolved or suspended in a mixture of propellent gas (for example chlorofluorohydrocarbons) can be used for administration as an inhalation spray. In this case it is preferable to use the active compound in micronized form, and one or more additional physiologically tolerated solvents can be present, for example ethanol. Inhalation solutions can be administered by means of customary inhalers. The new compounds can also by lyophilized, and the resulting lyophilizates can be used, for example, for the preparation of injection preparations. The formulations indicated can be sterilized and/or can contain auxiliaries, such as preservatives, stabilizers and/or wetting agents, emulsifiers, salts for influencing the osmotic pressure, buffer substances, colorants and/or aroma substances. If desired, they can also contain one or more further active compounds, for example one or more vitamins.

The substances according to the invention are, as a rule, administered analogously to other known, commercially available peptides, but, in particular, analogously to the compounds described in EP-A 249,096, preferably in dosages between about 10 mg and 1 g, in particular between 50 and 500 mg, per dosage unit. The daily dosage is preferably between about 0.2 and 20 mg/kg, in particular 1 and 10 mg/kg, of body weight. The particular dose for each given patient depends, however, on a very wide variety of factors, for example on the effectiveness of the particular compounds employed, on the age, body weight, general state of health, sex, diet, time and means of administration, on the excretion rate, the combination of medicaments and on the severity of the particular disease to which the therapy is applied. Parenteral administration is preferred.

Renin-dependent hypertension and hyperaldosteronism can be treated effectively by administering dosages between, in particular, about 1 and 300, preferably between 5 and 50, mg/kg of body weight. For diagnostic purposes the new compounds can preferably be administered in individual doses between about 0.1 to 10 mg/kg of body weight.

In the preceding and following text all the temperatures are quoted in °C. In the examples which follow "customary working up" means as follows: if necessary, water is added, the pH is adjusted to a value between 2 and 8 depending on the structure of the end product, the mixture is extracted with ethyl acetate or methylene dichloride, the phases are separated, the organic phase is dried over sodium sulfate and evaporated and the residue is purified by chromatography over silica gel and/or by crystallization.

Without further elaboration, it is believed that one skilled in the art can, using the preceding description, utilize the present intention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application P 38 40 289.0 filed in the Federal Republic of Germany, Nov. 30, 1988, are hereby incorporated by referene.

EXAMPLE 1

A mixture of 1088 mg of 3S-hydroxy-4S-[4-(2-pyrimidinyl)-piperazinocarbonyl-L-phenylalanyl-L-(imi-2,4-dinitrophenyl)-histidyl-amino]-5-cyclohexyl-pentanoyl-L-isoluecine-(N-4-amino-2-methyl-5-pyrimidinylmethylamide ["4-(2-pyrimidinyl)-piperazinocarbonyl-Phe-(imi)-DNP-His)-AHCP-Ile-AMPA"; obtainable by reacting 4-(2-pyrimidinyl)-piperazinocarbonyl chloride with H-Phe-OH in DMF/NaH to give 4-(2-pyrimidinyl)-piperazinocarbonyl-Phe-OH and subjecting the latter to a condensation reaction with H-(imi-DNP-His)-AHCP-Ile-AMPA], 2 g of 2-mercaptoethanol, 20 ml of DMF and 20 ml of water is stirred with aqueous $Na_2CO_3$ solution at 20° to adjust the pH to 8 and is then stirred for 2 hours at 20°. Working up in the customary manner gives 4-(2-pyrimidinyl)-piperazinocarbonyl-Phe-His-AHCP-Ile-AMPA, m.p. 216°.

The following are obtained analogously from the corresponding imi-DNP-His derivatives:

4-(2-pyrimidinyl)-piperazinocarbonyl-Phe-His-AHCP-AMPA
4-(2-pyrimidinyl)-piperazinocarbonyl-Phe-His-AHCP-Ile-ADAP
4-(2-pyrimidinyl)-piperazinocarbonyl-Phe-His-AHCP-Leu-AMAP
4-(2-pyrimidinyl)-piperazinocarbonyl-Phe-His-AHCP-Leu-ADPA
4-pyrrolidino-piperazinocarbonyl-Phe-His-AHCP-Ile-AMAP
4-pyrrolidino-piperidinocarbonyl-Phe-His-AHCP-Ile-ADPA
4-pyrrolidino-piperidinocarbonyl-Phe-His-AHCP-Leu-AMPA
4-pyrrolidino-piperidinocarbonyl-Phe-His-AHCP-Leu-ADPA
4-piperidino-piperidinocarbonyl-Phe-His-AHCP-Ile-AMPA
4-piperidino-piperidinocarbonyl-Phe-His-AHCP-Ile-ADPA
4-piperidino-piperidinocarbonyl-Phe-His-AHCP-Leu-AMPA
4-piperidino-piperidinocarbonyl-Phe-His-AHCP-Leu-ADPA.

EXAMPLE 2

10 g of 4-piperidino-benzoyl-Phe-(imi-BOM-His)-AHCP-Ile-AMPA [obtainable by reacting 4-piperidino-benzoyl-Phe-OH with H-(imi-BOM-His)-AHCP-Ile-AMPA] and 15 g of ammonium formate are dissolved in 200 ml of methanol, 10 g of 5% Pd-on-C are added and the mixture is stirred for 16 hours at 20°. Filtration and working up in the customary manner gives 4-piperidino-benzoyl-Phe-His-AHCP-Ile-AMPA

EXAMPLE 3

A mixture of 10 g of 4-phthalimidocyclohexylcarbonyl-Phe-Gly-AHCP-Ile-AMPA [obtainable by reacting 4-phthalimidocyclohexylcarbonyl chloride with H-Phe-Gly-AHCP-Ile-AMPA and separating the enantiomers by chromatography over silica gel], 0.55 g of hydrazine hydrate and 120 ml of ethanol is stirred for 24 hours at 20° and then evaporated. 1N hydrochloric acid is added, the mixture is filtered and the filtrate is worked up in the customary manner to give 4-aminocyclohexylcarbonyl-Phe-Gly-AHCP-Ile-AMPA, dihydrochloride, m.p. 232°.

4-Aminocyclohexylcarbonyl-D-Phe-Gly-AHCP-Ile-AMPA is obtained analogously from the enantiomeric 4-phthalimidocyclohexylcarbonyl-D-Phe-Gly-AHCP-Ile-AMPA.

4-Aminocyclohexylcarbonyl-Phe-βAla-AHCP-Ile-AMPA is obtained analogously from 4-phthalimidocyclohexylcarbonyl-Phe-βAla-AHCP-Ile-AMPA.

EXAMPLE 4

1.01 g of N-methylmorpholine is added to a solution in 60 ml of methylene dichloride of 6.39 g of H-Phe-Gly-AHCP-Ile-AMPA [obtainable by subjecting H-Gly-OMe to a condensation reaction with BOC-Phe-OH to give BOC-Phe-Gly-OMe, saponifying the latter and subjecting the product to a condensation reaction with H-AHCP-Ile-AMPA to give BOC-Phe-Gly-AHCP-Ile-AMPA and splitting off the BOC group]. 2.43 g of 4-BOC-aminocyclohexanecarbonylic acid, 1.35 g of HOBt and a solution of 2.06 g of DCCI in 50 ml of methylene dichloride are added with stirring, the mixture is stirred for 14 hours at 0°–10°, the precipitated dicyclohexylurea is filtered off and the manner gives 4-BOC-aminocyclohexylcarbonyl-Phe-Gly-AHCP-Ile-AMPA, m.p. 141°–143°.

The following are obtained analogously
4-CBZ-aminocyclohexylcarbonyl-Phe-Gly-AHCP-Ile-AMPA
4-BOC-aminocyclohexylcarbonyl-Phe-Gly-AHCP-Ile-ADPA
4-BOC-aminocyclohexylcarbonyl-Phe-Gly-AHCP-Leu-AMPA
4-BOC-aminocyclohexylcarbonyl-Phe-Gly-AHCP-Leu-ADPA
4-BOC-aminocyclohexylcarbonyl-Phe-βAla-AHCP-Ile-AMPA
4-BOC-aminocyclohexylcarbonyl-Phe-βAla-AHCP-Ile-ADPA
4-BOC-aminocyclohexylcarbonyl-Phe-βAla-AHCP-Leu-AMPA
4-BOC-aminocyclohexylcarbonyl-Phe-βAla-AHCP-Leu-ADPA.

EXAMPLE 5

4-(2-Pyrimidinyl)-piperazinocarbonyl-Phe-Gly-AHCP-Leu-AMPA, m.p. 125°, is obtained analogously to Example 4 from 4-(2-pyrimidinyl)-piperazinocarbonyl-Phe-OH and H-Gly-AHCP-Leu-AMPA. Trihydrochloride, m.p. 108°.

4-(2-Pyridyl)-piperazinocarbonyl-Phe-Gly-AHCP-Ile-AMPA is obtained analogously using 4-(2-pyridyl)-piperazinocarbonyl-Phe-OH. Dihydrochloride, m.p. 109° (dec.).

6-[4-(2-Pyrimidinyl)-piperazino]-hexanoyl-Phe-βAla-AHCP-Ile-AMPA is obtained analogously from 6-[4-(2-pyrimidinyl)piperazino]-hexanoyl-Phe-OH and H-βAla-AHCP-Ile-AMPA. Trihydrochloride, m.p. 214°.

4-(2-Pyrimidinyl)-piperazinocarbonyl-Phe-βAla-AHCP-Ile-AMPA is obtained analogously with 4-(2-Pyrimidinyl)-piperazinocarbonyl-Phe-OH. Trihydrochloride-monohydrate, m.p. 214°.

The following are obtained analogously:
4-pyrrolidinopiperidinocarbonyl-Phe-Gly-AHCP-Ile-AMPA
4-pyrrolidinopiperidinocarbonyl-Phe-Gly-AHCP-Ile-ADPA 4-pyrrolidinopiperidinocarbonyl-Phe-Gly-AHCP-Leu-AMPA
4-pyrrolidinopiperidinocarbonyl-Phe-Gly-AHCP-Leu-ADPA
4-pyrrolidinopiperidinocarbonyl-Phe-βAla-AHCP-Ile-AMPA
4-pyrrolidinopiperidinocarbonyl-Phe-βAla-AHCP-Ile-ADPA
4-pyrrolidinopiperidinocarbonyl-Phe-βAla-AHCP-Leu-AMPA
4-pyrrolidinopiperidinocarbonyl-Phe-βAla-AHCP-Leu-ADPA
4-piperidinopiperidinocarbonyl-Phe-Gly-AHCP-Ile-AMPA, dihydrochloride, m.p. 142° (decomposition)
4-piperidinopiperidinocarbonyl-Phe-Gly-AHCP-Ile-ADPA
4-piperidinopiperidinocarbonyl-Phe-Gly-AHCP-Leu-AMPA
4-piperidinopiperidinocarbonyl-Phe-Gly-AHCP-Leu-ADPA
4-piperidinopiperidinocarbonyl-Phe-βAla-AHCP-Ile-AMPA dihydrochloride, m.p. 126° (dec.)
4-piperidinopiperidinocarbonyl-Phe-βAla-AHCP-Ile-ADPA
4-piperidinopiperidinocarbonyl-Phe-βAla-AHCP-Leu-AMPA
4-piperidinopiperidinocarbonyl-Phe-βAla-AHCP-Leu-ADPA.

EXAMPLE 6

4-(2-Pyrimidinyl)-piperazinocarbonyl-Phe-βAla-AHCP-Leu-AMPA, m.p. 110°, is obtained analogously to Example 4 from 4-(2-pyrimidinyl)-piperazinocarbonyl-Phe-βAla-OH and H-AHCP-Leu-AMPA. Trihydrochloride, m.p. 86.5°.

EXAMPLE 7

4-Dimethylaminocyclohexylcarbonyl-Phe-Gly-AHCP-Ile-AMPA is obtained analogously to Example 4 from 4-dimethylaminocyclohexylcarbonyl-Phe-Gly-AHCP-OH and H-Ile-AMPA.

The following are obtained analogously:
4-dimethylaminocyclohexylcarbonyl-Phe-Gly-AHCP-Ile-ADPA
4-dimethylaminocyclohexylcarbonyl-Phe-Gly-AHCP-Leu-AMPA
4-dimethylaminocyclohexylcarbonyl-Phe-Gly-AHCP-Leu-ADPA
4-dimethylaminocyclohexylcarbonyl-Phe-βAla-AHCP-Ile-AMPA
4-dimethylaminocyclohexylcarbonyl-Phe-βAla-AHCP-Ile-ADPA
4-dimethylaminocyclohexylcarbonyl-Phe-βAla-AHCP-Leu-AMPA
4-dimethylaminocyclohexylcarbonyl-Phe-βAla-AHCP-Leu-ADPA
4-diethylaminocyclohexylcarbonyl-Phe-Gly-AHCP-Ile-AMPA
4-diethylaminocyclohexylcarbonyl-Phe-Gly-AHCP-Ile-ADPA
4-diethylaminocyclohexylcarbonyl-Phe-Gly-AHCP-Leu-AMPA
4-diethylaminocyclohexylcarbonyl-Phe-Gly-AHCP-Leu-ADPA
4-diethylaminocyclohexylcarbonyl-Phe-βAla-AHCP-Ile-AMPA
4-diethylaminocyclohexylcarbonyl-Phe-βAla-AHCP-Ile-ADPA
4-diethylaminocyclohexylcarbonyl-Phe-βAla-AHCP-Leu-AMPA
4-diethylaminocyclohexylcarbonyl-Phe-βAla-AHCP-Leu-ADPA
4-pyrrolidinocyclohexylcarbonyl-Phe-Gly-AHCP-Ile-AMPA
4-pyrrolidinocyclohexylcarbonyl-Phe-Gly-AHCP-Ile-ADPA
4-pyrrolidinocyclohexylcarbonyl-Phe-Gly-AHCP-Leu-AMPA
4-pyrrolidinocyclohexylcarbonyl-Phe-Gly-AHCP-Leu-ADPA
4-pyrrolidinocyclohexylcarbonyl-Phe-βAla-AHCP-Ile-AMPA
4-pyrrolidinocyclohexylcarbonyl-Phe-βAla-AHCP-Ile-ADPA
4-pyrrolidinocyclohexylcarbonyl-Phe-βAla-AHCP-Leu-AMPA
4-pyrrolidinocyclohexylcarbonyl-Phe-βAla-AHCP-Leu-ADPA
4-piperidino-cyclohexylcarbonyl-Phe-Gly-AHCP-Ile-AMPA
4-piperidino-cyclohexylcarbonyl-Phe-Gly-AHCP-Ile-ADPA
4-piperidino-cyclohexylcarbonyl-Phe-Gly-AHCP-Leu-AMPA
4-piperidino-cyclohexylcarbonyl-Phe-Gly-AHCP-Leu-ADPA
4-piperidino-cyclohexylcarbonyl-Phe-βAla-AHCP-Ile-AMPA
4-piperidino-cyclohexylcarbonyl-Phe-βAla-AHCP-Ile-ADPA
4-piperidino-cyclohexylcarbonyl-Phe-βAla-AHCP-Leu-AMPA
4-piperidino-cyclohexylcarbonyl-Phe-βAla-AHCP-Leu-ADPA.

EXAMPLE 8

4-BOC-aminocyclohexylcarbonyl-Phe-Gly-AHCP-Ile-Ala-(N-3-pyridylmethylamide) is obtained analogously to Example 4 from 4-BOC-aminocyclohexylcarbonyl-Phe-Gly-AHCP-Ile-OH and H-Ala-(N-3-pyridylmethylamide).

EXAMPLE 9

2-(1-Naphthylmethyl)-3-[4-(2-pyrimidinyl)-piperazinocarbonyl]-propionyl-Gly-AHCP-Ile-AMPA, m.p. 155°, is obtained analogously to Example 4 from 2-(1-naphthylmethyl)-3-[4-(2-pyrimidinyl)-piperazinocarbonyl]-propionyl-Gly-AHCP-Ile-OH and 2-methyl-4-amino-5-aminomethylpyrimidine ("H-AMPA").

The following are obtained analogously:
4-BOC-aminocyclohexylcarbonyl-Phe-Gly-AHCH-Ile-NH$_2$
4-BOC-aminocyclohexylcarbonyl-Phe-Gly-AHPP-Ile-(N-methylamide)
4-BOC-aminocyclohexylcarbonyl-Phe-Gly-Sta-Ile-(N,N-dimethylamide)
4-BOC-aminocyclohexylcarbonyl-Phe-Gly-AHCP-Abu-AMPA
4-BOC-aminocyclohexylcarbonyl-Phe-Gly-AHCP-Ala-AMPA
4-BOC-aminocyclohexylcarbonyl-Phe-Gly-AHCP-Cal-AMPA
4-BOC-aminocyclohexylcarbonyl-Phe-Gly-AHCP-Leu-AMPA 4-BOC-aminocyclohexylcarbonyl-Phe-Gly-AHCP-Met-AMPA
4-BOC-aminocyclohexylcarbonyl-Phe-Gly-AHCP-Nle-AMPA
4-BOC-aminocyclohexylcarbonyl-Phe-Gly-AHCP-Nva-AMPA
4-BOC-aminocyclohexylcarbonyl-Phe-Gly-AHCP-Phe-AMPA
4-BOC-aminocyclohexylcarbonyl-Phe-Gly-AHCP-Trp-AMPA
4-BOC-aminocyclohexylcarbonyl-Phe-Gly-AHCP-Tyr-AMPA
4-BOC-aminocyclohexylcarbonyl-Phe-Gly-AHCP-Val-AMPA
4-BOC-aminocyclohexylcarbonyl-Phe-Gly-AHCP-Ile-(N-2-pyridylmethylamide)
4-BOC-aminocyclohexylcarbonyl-Phe-Gly-AHCP-Ile-(N-3-pyridylmethylamide)
4-BOC-aminocyclohexylcarbonyl-Phe-Gly-AHCP-Ile-(N-m-aminomethylbenzylamide)
4-BOC-aminocyclohexylcarbonyl-Phe-Gly-AHCP-Ile-(N-2-hydroxy-4,6-dimethyl-5-pyridylmethylamide)
4-BOC-aminocyclohexylcarbonyl-Phe-Gly-AHCP-Ile-(p-sulfamoylanilide).

EXAMPLE 10

A mixture of 8 g of 2-chloroethylmercaptoacetyl-Phe-Gly-AHCP-Ile-ADPA (obtainable from 2-chloroethylmercaptoacetyl chloride and H-Phe-Gly-AHCP-Ile-ADPA), 1 g of dimethylamine and 150 ml of THF is shaken in a closed apparatus for 1 hour at 20°. Working up in the customary manner gives 2-dimethylaminoethylmercaptoacetyl-Phe-Gly-AHCP-Ile-ADPA, dihydrochloride, m.p. 165° (decomposition).

The following are obtained analogously:
2-diethylaminoethylmercaptoacetyl-Phe-Gly-AHCP-Ile-AMPA
2-diethylaminoethylmercaptoacetyl-Phe-Gly-AHCP-Ile-ADPA
2-diethylaminoethylmercaptoacetyl-Phe-Gly-AHCP-Leu-AMPA
2-diethylaminoethylmercaptoacetyl-Phe-Gly-AHCP-Leu-ADPA
2-diethylaminoethylmercaptoacetyl-Phe-βAla-AHCP-Ile-AMPA
2-diethylaminoethylmercaptoacetyl-Phe-βAla-AHCP-Ile-ADPA
2-diethylaminoethylmercaptoacetyl-Phe-βAla-AHCP-Leu-AMPA
2-diethylaminoethylmercaptoacetyl-Phe-βAla-AHCP-Leu-ADPA.

EXAMPLE 11

4-Aminocyclohexylcarbonyl-Phe-Gly-AHCP-Ile-AMPA, dihydrochloride, m.p. 232°, is obtained from 4-bromo-cyclohexylcarbonyl-Phe-Gly-AHCP-Ile-AMPA (obtainable from 4-bromo-cyclohexylcarbonyl chloride and H-Phe-Gly-AHCP-Ile-AMPA) by means of excess NH₃ in THF.

EXAMPLE 12

A mixture of 1.27 g of the Na salt of 2-dimethylaminoethylmercaptan, 7.41 g of chloroacetyl-Phe-Gly-AHCP-Ile-ADPA (obtainable from chloroacetyl chloride and H-Phe-Gly-AHCP-Ile-ADPA) and 120 ml of absolute ethanol is boiled for 1 hour with stirring. The mixture is cooled, the precipitated NaCl is filtered off and the filtrate is worked up in the customary manner to give 2-dimethylaminoethylmercaptoacetyl-Phe-Gly-AHCP-Ile-ADPA, dihydrochloride, m.p. 165° (decomposition).

The following are obtained analogously:
2-diethylaminoethylmercaptoacetyl-Phe-Gly-AHCP-Ile-AMPA
2-diethylaminoethylmercaptoacetyl-Phe-Gly-AHCP-Leu-AMPA
2-diethylaminoethylmercaptoacetyl-Phe-Gly-AHCP-Leu-ADPA
2-diethylaminoethylmercaptoacetyl-Phe-βAla-AHCP-Ile-AMPA
2-diethylaminoethylmercaptoacetyl-Phe-βAla-AHCP-Ile-ADPA
2-diethylaminoethylmercaptoacetyl-Phe-βAla-AHCP-Leu-AMPA
2-diethylaminoethylmercaptoacetyl-Phe-βAla-AHCP-Leu-ADPA

EXAMPLE 13

A mixture of 1.64 g of 1-(2-pyrimidinyl)-piperazine, 1.01 g of N-methylmorpholine, 8.29 g of 6-bromohexanoyl-Phe-Gly-AHCP-Ile-AMPA (obtainable from 6-bromohexanoyl chloride and H-Phe-Gly-AHCP-Ile-AMPA) and 150 ml of THF is boiled for 1 hour with stirring. The mixture is filtered and filtrate is worked up in the customary manner to give 6-[4-(2-pyrimidinyl)-piperazino]-hexanoyl-Phe-Gly-AHCP-Ile-AMPA, m.p. 142°. Trihydrochloride-dihydrate, m.p. 161°–163°.

EXAMPLE 14

A solution of 10 g of 4-BOC-aminocyclohexylcarbonyl-Phe-Gly-AHCP-Ile-AMPA in 200 ml of 4N HCl in dioxane is stirred for 40 minutes at 20° and is then evaporated. This gives 4-aminocyclohexylcarbonyl-Phe-Gly-AHCP-Ile-AMPA dihydrochloride, m.p. 232°.

The following are obtained analogously:
4-aminocyclohexylcarbonyl-Phe-Gly-AHCP-Ile-ADPA
4-aminocyclohexylcarbonyl-Phe-Gly-AHCP-Leu-AMPA
4-aminocyclohexylcarbonyl-Phe-Gly-AHCP-Leu-ADPA
4-aminocyclohexylcarbonyl-Phe-βAla-AHCP-Ile-AMPA
4-aminocyclohexylcarbonyl-Phe-βAla-AHCP-Ile-ADPA
4-aminocyclohexylcarbonyl-Phe-βAla-AHCP-Leu-AMPA
4-aminocyclohexylcarbonyl-Phe-βAla-AHCP-Leu-ADPA.

EXAMPLE 15

1 g of 4-CBZ-aminocyclohexylcarbonyl-Phe-Gly-AHCP-Ile-AMPA is dissolved in 25 ml of ethanol and hydrogenated over 0.5 g of 10% Pd-on-C at 20° and 1 bar until absorption of H₂ ceases; the mixture is filtered and the filtrate is evaporated to give, after purification by chromatography, 4-aminocyclohexylcarbonyl-Phe-Gly-AHCP-Ile-AMPA; dihydrochloride, m.p. 232°.

EXAMPLE 16 a) 3-Oxo-4S-(6-[4-(2-pyrimidinyl)-piperazino]-hexanoyl-Phe-Gly-amino)-5-cyclohexylpentanoyl-Ile-AMPA is obtained analogously to Example 4 from 6-[4-(2-pyrimidinyl)-piperazino]-hexanoyl-Phe-Gly-OH and 3-oxo-4S-amino-5-cyclohexylpentanoyl-Ile-AMPA.

b) A solution of 1 of the above ketoamide in 25 ml of CH₃OH is hydrogenated over 0.1 g of 10% Pd-on-C at 20° and 1 bar until absorption of H₂ ceases. The filtration and evaporation of the filtrate give a mixture of 3R- and 3S-hydroxy-4S-(6-[4-(2-pyrimidinyl)-piperazino]-hexanoyl-Phe-Gly-amino)-5-cyclohexylpentanoyl-Ile-AMPA (m.p. 142°; "6-[4-(2-pyrimidinyl)-piperazino]-hexanoyl-Phe-Gly-AHCP-Ile-AMPA) which can be separated by chromatography.

EXAMPLE 17

70 mg of hydroxylamine hydrochloride are added to a solution of 754 mg o the ketoamide obtainable in accordance with Example 16a, and 1.43 g of Na₂CO₃.10 H₂O in 5 ml of methanol and 5 ml of water, and the mixture is stirred for 14 hours at 20°. The precipitated oxime is filtered off, dried, dissolved in 10 ml of methanol and hydrogenated over 0.5 g of Raney nickel at 20° and 5 bar. The catalyst is filtered off, the filtrate is evaporated and the resulting mixture is separated over silica gel to give 3S-amino-4S-(6-[4-(2-pyrimidinyl)-piperazino]-hexanoyl-Phe-Gly-amino)-5-cyclohexyl-pentanoyl-Ile-AMPA (=6-[4-(2-pyrimidinyl)-piperazino]-hexanoyl-Phe-Gly-DACP-Ile-AMPA); the 3R-amino epimer is obtained additionally.

The following examples relate to pharmaceutical formulations.

EXAMPLE A

Tablets

A mixture of 1 kg of 4-aminocyclohexylcarbonyl-Phe-Gly-AHCP-Ile-AMPA dihydrochloride, 4 kg of lactose, 1.2 kg of maize starch, 200 g of talc and 100 g magnesium stearate is compressed in a customary manner to give tablets, so that each tablet contains 100 mg of active compound.

EXAMPLE B

Coated tablets

Tablets are compressed analogously to Example A and are then coated in a customary manner with a coating composed of sucrose, maize starch, talc, tragacanth and colorant.

EXAMPLE C

Capsules 500 g of 4-aminocyclohexylcarbonyl-Phe-βAla-AHCP-Ile-AMPA dihydrochloride are filled into hard gelatine capsules in a customary manner so that each capsule contains 500 mg of active compound.

EXAMPLE D

Vials

The pH of a solution of 100 g of 2-dimethylaminoethylmercaptoacetyl-Phe-Gly-AHCP-Ile-ADPA dihydrochloride in 4 l of twice-distilled water is adjusted to 6.5 with 2N hydrochloric acid, and the solution is filtered under sterile conditions and filled into vials. The product is lyophilized under sterile conditions and sealed so as to be sterile. Each vial contains 50 mg of active compound.

EXAMPLE E

Suppositories

A mixture of 50 g of 4-(2-pyrimidinyl)-piperazinocarbonyl-Phe-Gly-AHCP-Leu-AMPA and 10 g of soya lecithin and 140 g of cocoa butter is melted, poured into moulds and allowed to cool. Each suppository contains 250 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An amino acid derivative of the formula $$R^1-Z-NR^2-CHR^3-CR^4-(CHR^5)_a-CO-E-Q-Y$$

wherein
  $R^1$ is $R^7-CO-$ or $R^7-CO-CH_2-CH(naphthyl-CH_2)-CO-$;
  Z is Phe-His, Phe-Gly, Phe-βAla, or Gly;
  E is Ile or Leu;
  Q—Y is —NH—CH₂—(4-amino-2-methyl-5-pyrimidinyl) or —NH—CH₂—(2-amino-5,6-dimethyl-3-pyrazinyl);
  $R^2$ is H;
  $R^3$ is cyclohexyl;
  $R^4$ is H and OH;
  —(CHR⁵)ₐ— is —CH₂—;
  $R^7$ is 4-(pyrimidinyl)-piperazino-$C_nH_{2n}$, 4-($R^{10}$NH)-cyclohexyl, 4-(pyridyl)-piperazino, 4-piperidinopiperidino, or A₂N—(CH₂)₂—S—CH₂—;
  $R^{10}$ is H or A—O—CO;
  A is alkyl having 1–4 C atoms; and
  n is 0, 1, 2, 3, 4 or 5; or physiologically acceptable salts thereof.

2. a) 4-aminocyclohexylcarbonyl-Phe-Gly-AHCP-Ile-AMPA; or b) 4-aminocyclohexylcarbonyl-Phe-βAla-AHCP-Ile-AMPA, each of a compound of claim 1.

3. A compound according to claim 1, wherein said compound is of the subformula $$R^7-CO-Z-W-E-Q-Y$$

and wherein W is —NR²—CHR³CR⁴—(CHR⁵)ₐ—CO—.

4. A compound according to claim 1, wherein said compound is of the subformula $$R^7-CO-CH_2-CH(naphthyl-CH_2)-CO-Z-W-E-Q-Y$$

and wherein W is —NR²—CHR³—CR⁴—(CHR⁵)ₐ—CO—.

5. A compound according to claim 1, wherein said compound is of the subformula $$A_2N-(CH_2)_2-S-CH_2-CO-Z-W-E-Q-Y$$

and wherein W is
  —NR²—CHR³—CR⁴—(CHR⁵)ₐ—CO—.

6. A compound according to claim 1, wherein said compound is of the subformula 4-($R^{10}$NH)-cyclohexyl—CO—Z—W—E—Q—Y and wherein W is
—$NR^2$—$CHR^3$—$CR^4$—$(CHR^5)_a$—CO—.

7. A compound according to claim 1, wherein said compound is of the subformula 4-aminocyclohexylcarbonyl-Z—W—E—Q—Y and wherein W is —$NR^2$—$CHR^3$—$CR^4$—$(CHR^5)_a$—CO—.

8. A compound according to claim 1, wherein said compound is of the subformula 4-piperidino-piperidino-CO—Z—W—E—Q—Y and wherein W is
—$NR^2$—$CHR^3$—$CR^4$—$(CHR^5)_a$—CO—.

9. A compound according to claim 1, wherein said compound is of the subformula 4-(pyrimidinyl)-piperazino-$C_nH_{2n}$—CO—Z—W—E—Q—Y or 4-(pyridyl)-piperazino-CO—Z—W—E—Q—Y and wherein W is —$NR^2$—$CHR^3$—$CR^4$—$(CHR^5)_a$—CO—.

10. A compound according to claim 1, wherein said compound is of the subformula 4-(2-pyrimidinyl)-piperazino-$C_nH_{2n}$—CO—Z—W—E—Q—Y and wherein W is
—$NR^2$—$CHR^3$—$CR^4$—$(CHR^5)_a$—CO—.

11. A pharmaceutical composition comprising a compound of claim 1 and a pharmaceutically acceptable carrier.

12. A pharmaceutical composition comprising about 10 mg-1 g of a compound of claim 1 and a pharmaceutically acceptable carrier.

13. A pharmaceutical composition comprising about 50-500 mg of a compound of claim 1 and a pharmaceutically acceptable carrier.

14. A method of treating renin-dependent hypertension or hyperaldosteronism comprising administering a compound of claim 1.

15. A method according to claim 14, comprising administering doses of said compound in an amount of about 1-300 mg/kg of body weight.

16. A method of treating renin-dependent, cardiac insufficiency comprising administering a compound of claim 1.

17. A method according to claim 16, comprising administering daily doses of said compound in an amount of about 0.2-20 mg/kg of body weight.

18. A method according to claim 16, comprising administering daily doses of said compound in an amount of about 1-10 mg/kg of body weight.

* * * * *